United States Patent [19]

Uchiyama

[11] 4,267,110
[45] May 12, 1981

[54] PROCESS FOR PREPARING DIBENZYLIDENESORBITOL AND COMPOSITION CONTAINING THE SAME

[75] Inventor: Hiroshi Uchiyama, Hirakata, Japan

[73] Assignees: E.C. Chemical Ind. Co., Ltd.; C. Itoh & Co., Ltd., both of Osaka, Japan

[21] Appl. No.: 70,833

[22] Filed: Aug. 29, 1979

[30] Foreign Application Priority Data

Nov. 29, 1978 [JP]  Japan .................................. 53-146587
May 30, 1979 [JP]  Japan .................................. 54-661036

[51] Int. Cl.³ ........................................... C07D 319/04
[52] U.S. Cl. .............................. 260/340.7; 260/30.4 R
[58] Field of Search ..................................... 260/340.7

[56] References Cited

U.S. PATENT DOCUMENTS 3,721,682  3/1973  Murai et al. ........................ 260/340.7
4,031,112  6/1977  Oppenlaender et al. .......... 260/340.7

FOREIGN PATENT DOCUMENTS 48-43748  12/1973  Japan .................................... 260/340.7

OTHER PUBLICATIONS

Chem. Abstracts 84:P45604a.
Chem. Abstracts 86:173395m.

*Primary Examiner*—Ethel G. Love
*Attorney, Agent, or Firm*—Wenderoth, Lind & Ponack

[57] ABSTRACT

In a process for preparing dibenzylidenesorbitol by dehydrocondensation of 1 mol of sorbitol with 2 mols of benzaldehyde in the presence of an acid catalyst, the improvement in which the reaction is carried out in two stages, the first-stage reaction comprising reacting the reactants with heating at a temperature of 50° to 70° C., the first-stage reaction being shifted to the second-stage reaction by adding water and an additional amount of an acid catalyst when the conversion of sorbitol to dibenzylidenesorbitol reaches 10 to 40%, and the second-stage reaction comprising of reacting the mixture in the suspended state at ordinary temperature in 2.5 or more parts by weight, per part by weight of sorbitol, of an aqueous reaction medium, and the resulting dibenzylidenesorbitol is obtained as an aqueous suspension.

5 Claims, 1 Drawing Figure

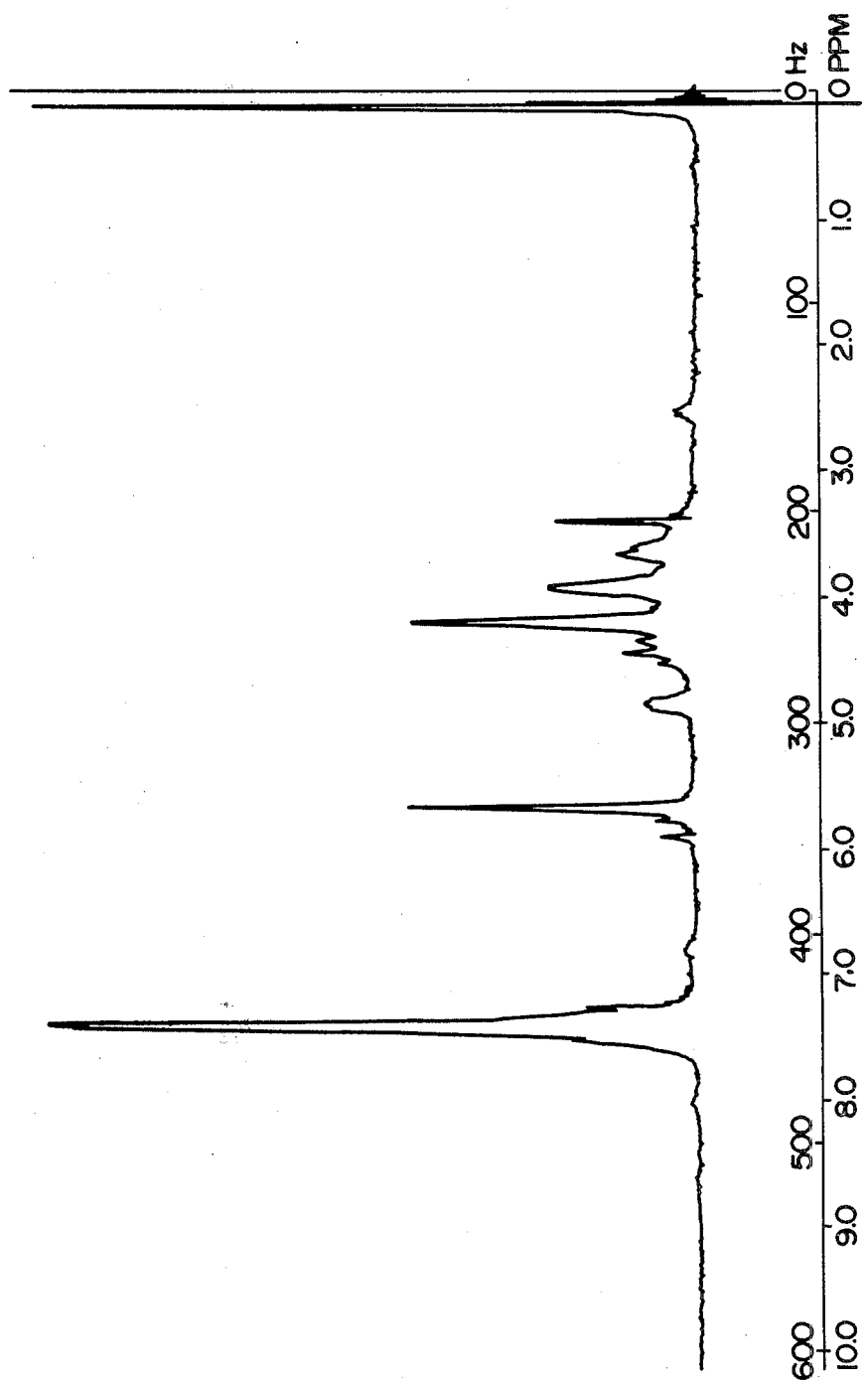

PROCESS FOR PREPARING DIBENZYLIDENESORBITOL AND COMPOSITION CONTAINING THE SAME

This invention relates to an improvement in a process for preparing dibenzylidenesorbitol (hereinafter referred to as DBS), and specifically, to an improvement in a process for obtaining DBS by dehydrocondensation of sorbitol and benzaldehyde in the presence of an acid catalyst. The invention is also concerned with a polyolefin composition having incorporated therein DBS containing tribenzylidenesorbitol as a by-product, said DBS being obtained by the process of the invention.

DBS is a useful substance as an agent for gelling organic liquids or as an agent for clarifying polyolefin resins. DBS is the product of dehydrocondensation between 1 mol of sorbitol and 2 mols of benzaldehyde. So far, DBS has been prepared by a process which comprises reacting benzaldehyde with a concentrated aqueous solution of sorbitol for a long time at ordinary temperature or with heating in the presence of sulfuric acid as a catalyst. According to this process, large amounts of monobenzylidenesorbitol (hereinafter referred to as MBS), and in some cases, of tribenzylidenesorbitol (hereinafter referred to as TBS) are formed as by-products, and the reaction product solidifies, thus making it necessary to pulverize the reaction product in the reactor in order to carry out subsequent steps such as neutralization of the acid catalyst and removal of the by-product. Thus, this process has been very inefficient.

Recently, a process has been proposed which comprises adding a large amount of cyclohexane to a reaction system consisting of an aqueous solution of sorbitol and benzaldehyde, performing the reaction under azeotropy of cyclohexane and water present in the aqueous solution of sorbitol and water formed by the condensation reaction, and causing the reaction to proceed while separating water from the reaction system for removal, thereby to obtain the reaction product as a slurry in which the medium is cyclohexane (Japanese Patent Publication No. 43748/73). This process, however, cannot avoid the formation of a considerable amount of MBS and a tiny amount of TBS as by-products, in addition to the formation of DBS.

Of those by-products, MBS adversely affects the aforementioned uses of DBS, especially its use as a clarifier for polyolefins. Hence, MBS must be removed, but its removal requires purification which is complicated and difficult to perform. It is also necessary to separate and recover the organic reaction medium and water, thereby causing the disadvantage that the steps involved become more complicated.

An object of the present invention, therefore, is to provide a process for the preparation of DBS in which MBS is not formed, or is hardly formed, as a by-product.

Another object of the present invention is to provide a process for the preparation of DBS wherein the reaction product is afforded in the slurry form without the need to use an organic reaction medium.

A further object of the present invention is to provide additives which do no harm to the effect of DBS for clarification of polyolefins and which facilitate the uniform mixing of DBS and polyolefins.

The present inventor has made studies for attainment of the abovementioned objects, and found that by performing the initial stage of the reaction of sorbitol with benzaldehyde in the presence of an acid catalyst while heating the reaction system at a temperature of 50° to 70° C., and when the conversion of sorbitol to DBS has reached 10 to 40%, adding a large amount of an aqueous reaction medium and an additional amount of an acid catalyst and lowering the reaction temperature to ordinary temperature, followed by conducting the subsequent stage of the reaction at ordinary temperature, the reaction product can be obtained as a slurry containing water as its medium, and the reaction product contains no, or virtually no, MBS which is conventionally formed as a by-product.

The present inventor has also found that DBS obtained by the process of the present invention contains TBS formed as a by-product, the ratio in weight of the TBS to the DBS being 10:90–35:65, and that the TBS-containing DBS, as contrasted with TBS-free high-purity DBS, is easily compatible with polyolefins and uniformly mixes therewith, said TBS doing no harm to the DBS action of improving the clarity of the polyolefins.

Specifically, the present invention is an improved process for preparing dibenzylidenesorbitol by dehydrocondensation of 1 mol of sorbitol with 2 moles of benzaldehyde in the presence of an acid catalyst, wherein the reaction is carried out in two stages, the first-stage reaction comprising of reacting the reactants with heating at a temperature of 50° to 70° C., the first-stage reaction being shifted to the second-stage reaction by adding water and an additional amount of an acid catalyst when the conversion of sorbitol to dibenzylidenesorbitol reaches 10 to 40%, and the second-stage reaction comprising reacting the mixture in the suspended state at ordinary temperature in 2.5 or more parts by weight, per part by weight of sorbitol, of an aqueous reaction medium, and the resulting dibenzylidenesorbitol is obtained as an aqueous suspension.

The fundamental reaction of the process of the present invention is the dehydrocondensation reaction of 1 mol of sorbitol with 2 moles of benzaldehyde in the presence of an acid catalyst and can be expressed by the following reaction scheme:

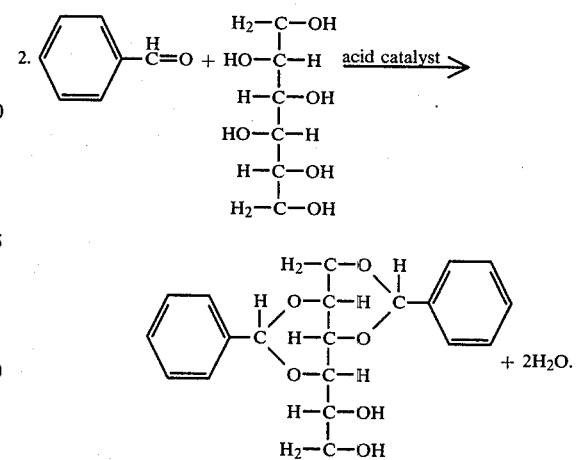

The process of the present invention is extremely characteristic, compared with conventional processes, in that the above reaction is performed in two stages including a stage in which the reaction is carried out in the suspended stage in a large amount of an aqueous reaction medium (second stage).

In the first stage of the reaction, the reaction of sorbitol with benzaldehyde is carried out at 50° to 70° C., preferably at 60° to 65° C., in the presence of an acid catalyst. When the conversion of sorbitol to DBS reaches 10 to 40%, preferably 20 to 30%, as a result of the reaction, a large amount of water is added as a reaction medium for shifting the reaction to the second stage. The amount of water added is such that the amount of water in the reaction system becomes 2.5 or more parts by weight, preferably 3 to 5 parts by weight, per part by weight of sorbitol charged. At the time of said addition of water, an additional amount of an acid catalyst is also added. Immediately after the shift to the second-stage reaction, the reaction temperature is lowered to ordinary temperature (15° to 25° C.), and the second-stage reaction is continued in the suspended state with water as a medium.

In the present invention, the conversion of sorbitol to DBS is the percentage of the weight of DBS formed based on the weight of the theoretical amount of DBS obtainable from sorbitol charged.

The amount of the aqueous reaction medium made present in the second-stage reaction includes the amount of condensation water formed by the reaction. If sorbitol or the acid catalyst is used as an aqueous solution, said amount includes the amount of water of this aqueous solution.

The first-stage reaction of the present invention is similar to the reaction of the conventional process in which a concentrated (70% or higher) aqueous solution of sorbitol and benzaldehyde are blended and reacted in the presence of an acid catalyst. If the first-stage reaction is continued without shift to the second-stage reaction, the reaction system will become markedly viscous and finally solidify, thereby impeding the advance of the reaction. The time when the first-stage reaction is shifted to the second-stage reaction in the present invention corresponds to the time before such marked viscosity is reached. The second-stage reaction proceeds in the suspended state in which the reaction system is finely dispersed in a large amount of an aqueous medium.

After the conversion of sorbitol to DBS in the first-stage reaction has exceeded the 40% limit specified in the present invention, the reaction system becomes markedly viscous or solidifies, thus making it difficult to shift the first-stage reaction to the second-stage reaction, and even if the shift to the second-stage reaction is forcibly carried out, there will be a considerable impediment to the advance of the reaction. If the shift to the second-stage reaction is performed before said conversion reaches 10%, on the other hand, the second-stage reaction will take a very long time to complete.

If the amount of the aqueous reaction medium in the second-stage reaction is too small, it will become impossible to maintain the reaction system suspended in the aqueous solution. If the aqueous reaction medium is used in an amount more than the necessary amount to maintain the reaction system in the suspended state, on the other hand, there will be no additional marked advantages.

If the reaction temperature in the first-stage reaction is too high, the resulting product will be colored, but if it is too low, the reaction will require a considerably long time to complete. Also, if the reaction at the second stage is performed with heating, there will be a decrease in the yield of DBS.

In the present invention, sorbitol is subjected to the reaction usually as a concentrated aqueous solution having a concentration of 70% or higher. It is also possible, however, to supply sorbitol as a solid powder.

In the present invention, 2 mols of benzaldehyde is used per mol of sorbitol. Benzaldehyde may be employed in an amount a little larger or smaller than 2 mols, and usually, its amount is within the range of 1.6 to 2.3 mols.

In the present invention, any acid can be used as a catalyst. Examples of the acid catalyst are inorganic acids such as sulfuric acid, hydrochloric acid and phosphoric acid, and organic acids such as p-toluenesulfonic acid and hexahydrophthalic anhydride.

The amount of the acid catalyst used in the first-stage reaction is 0.03 to 0.5 part by weight, preferably 0.04 to 0.08 part by weight, per part by weight of sorbitol. In the second-stage reaction, the acid catalyst is further added in an amount of 0.02 to 0.5 part by weight, preferably 0.06 to 0.1 part by weight, per part by weight of sorbitol.

As described above, the acid catalyst needs to be divided into portions used for the first-stage reaction and the second-stage reaction. The addition of the total amount of the acid catalyst to the first-stage reaction would result in the decrease in the yield of the product. The acid catalyst used in the first-stage and second-stage reactions may be different or the same in type between these reactions.

The acid catalyst is usually used as an aqueous solution, and preferably used in the first-stage reaction as a concentrated aqueous solution having a concentration of 50% or higher. An organic acid such as p-toluenesulfonic acid or hexahydrophthalic anhydride, however, can be used in the first-stage reaction as it is without being made into an aqueous solution.

Preferably, the reaction of the present invention is carried out in an inert gas atmosphere such as nitrogen, but it may be performed in air or at ordinary pressure or with application of pressures.

The reaction of the present invention is made to proceed satisfactorily by performing it with stirring throughout the respective stages of the reaction. In the reaction at the first stage, as the reaction proceeds, the viscosity of the reaction mixture increases gradually. Hence, it is advisable to judge the end point of the first-stage reaction by the torque which the stirrer requires for stirring. The time when the torque of the stirrer increases to about 3 times that present at the initiation of the reaction corresponds to the time when the conversion of sorbitol to DBS reaches about 20 to 25%. Usually, this state is attained about 20 to 90 minutes after initiation of the reaction.

In the second-stage reaction, DBS being formed with the progress of the reaction precipitates in the aqueous medium as a solid fine powder and becomes suspended. Accordingly, suspended matter gradually increases in amount, the viscosity of the suspension increases, and finally, the state is attained in which the suspended condition will not break upon the stoppage of stirring. At this time, the second-stage reaction is terminated. The time required for the completion of the second-stage reaction is about 6 to 8 hours.

The reaction product at the end point of the second-stage reaction is obtained as a suspension in which a crude DBS powder is dispersed finely in the aqueous reaction medium. Thus, the reaction product can be easily neutralized, filtered off, washed with water and dried to recover DBS. Its yield is usually about 60 to 65%.

The above-mentioned suspension may be further allowed to stand for about 12 hours for aging, then filtered off, neutralized, washed with water and dried. This aging enables the yield of DBS to be increased to about 75 to 80%.

The process of the present invention needs no use of an organic solvent in any stage of the process, and the process permits powdery DBS of a constant quality to be obtained easily and inexpensively.

NMR analysis has shown that DBS recovered in the above-described manner contains no MBS and comprises 90 to 65 parts by weight of DBS and 10 to 35 parts by weight of TBS formed as a by-product. The attached drawing shows the NMR spectrum of the recovered DBS. This product has a melting point of about 182° to 187° C. This product can be added, without any purification, to polyolefin resins, with the result that shaped articles or sheets produced from the blends can have an improved clarity. These shaped articles or sheets are advantageous in hygiene of foods because even when they are treated with hot water, MBS never comes out.

The present inventor previously found that the addition of DBS to polyolefins affords polyolefin compositions having markedly improved clarity which are free from the drawbacks caused by the conventional additives (Japanese Patent Application No. 94424/74).

DBS, however, has a high melting point (about 210° C.) and its compatibility with polyolefins is not entirely satisfactory.

The present inventor has now found that DBS containing therein a small amount of TBS has improved compatibility with polyolefins.

The present invention, therefore, provides an improved resin composition containing one or more polymers or copolymers of aliphatic monoolefins and dibenzylidenesorbitol as essential ingredients, said composition further containing tribenzylidenesorbitol.

TBS-containing DBS favorably improves the clarity of olefin polymers and favorably reduces their shrinkage when they are molded (molding shrinkage). Examples of such olefin polymers include polymers or copolymers of aliphatic monoolefins having 2 to 6 carbon atoms, said polymers or copolymers having number-average molecular weights of about 10,000 to 200,000, preferably about 30,000 to 150,000. Specific examples of the polymers or copolymers are polyethylene, polypropylene, crystalline copolymers of ethylene and propylene, and polymethylpentene.

The polyolefins exemplified above are basically linear regular polymers which in some cases have short side chains.

High-purity DBS is a white powder having a melting point of 210° to 212° C. It is expressed by the following chemical formula (I)

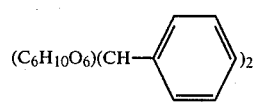

and exists mainly as three types of isomers. Its typical structural formula is the following formula (II):

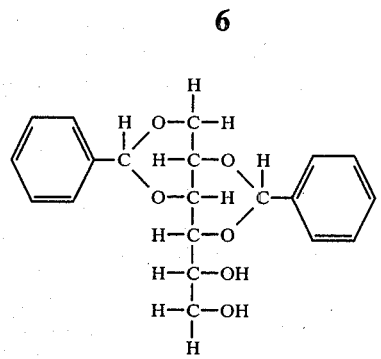

TBS can be prepared by reacting DBS further with 1 mol of benzaldehyde with heating in the presence of an acid catalyst. The so prepared TBS is a white powder having a melting point of about 189° to 191° C. It is expressed by the following chemical formula

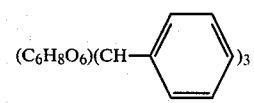

and its structure is expressed by the following formula (IV).

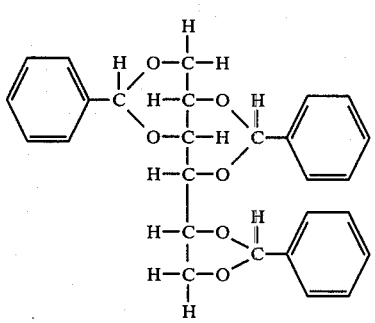

The content of DBS in the composition of the present invention is in the range of 0.1 to 0.7% by weight, preferably 0.3 to 0.5% by weight, based on the total amount of the composition. A DBS content less than 0.1% by weight does not afford sufficient clarity or a reduction in the molding shrinkage of the resulting composition. A DBS content of more than 0.7% by weight would not give additional advantages, though it is possible to incorporate DBS in an amount of more than 0.7% by weight. It is also possible to form a concentrated composition containing DBS in a large amount of up to about 4% by weight and to use it as a masterbatch.

TBS is used in a weight ratio to DBS of 5:95–50:50, preferably 10:90–40:60. If the ratio of TBS to DBS is too low, uniform mixing of DBS with polyolefins becomes difficult. The use of TBS in an excessively large amount compared with DBS, on the other hand, would not give any additional marked advantages.

Predetermined amounts of DBS and TBS within the range set forth above can be added to a polyolefin separately in an arbitrary order. Simultaneous addition of DBS and TBS to the polyolefin, however, is preferred; in this case, DBS and TBS may be first mixed together and then added to the polyolefin.

The most suitable procedure is to use the aforementioned DBS containing no MBS and containing a small amount of by-product TBS as obtained by the process of the present invention.

According to the conventional process for producing DBS, the resulting DBS contains a considerable amount of MBS, thus requiring troublesome purification for removal of the MBS. DBS obtained by the process of the present invention does not need such purification, and contains by-product TBS in a weight ratio, to the DBS, of about 10:90–35:65. The by-product TBS-containing DBS obtained by the process of the present invention, therefore, is suitable as it is for use as the additive of the present invention.

The composition of the present invention can be obtained by adding predetermined amounts of DBS and TBS or a predetermined amount of a mixture of these to the olefin polymer or copolymer that has been exemplified earlier, and mixing them by an arbitrary mixing means.

It is possible to add to the composition of the present invention other additives, e.g., transparent colorants and plasticizers such as dioctyl phthalate, dibutyl phthalate, dioctyl stearate and dioctyl adipate, unless these additives adversely affect the clarity and/or the molding shrinkage of the composition.

Since the composition of the present invention provides films, sheets, and hollow molded articles having improved clarity, reduced molding shrinkage, and excellent mechanical and chemical properties, it is preferred as a packaging material for cosmetics and foods, and as material for making containers.

The present invention will be described in more detail by reference to the examples below. In the examples, parts and percents are by weight unless otherwise specified.

In the examples, values of clarity (haze value) and of molding shrinkage are obtained by the following methods:

(1) Haze value ... ASTM D1001-59T
(2) Molding shrinkage

A test piece is prepared by injection molding a resin composition at a predetermined injection molding temperature with the use of a mold having a cavity in the shape of a rectangle 55 mm long and 10 mm × 10 mm in cross section. The test piece is measured for thickness, and its shrinkage is calculated from the following equation:

$$\text{Shrinkage} = \frac{\text{Depth of cavity of mold} - \text{Thickness of test piece}}{\text{Depth of cavity of mold}} \times 100(\%)$$

Injection molding of the test piece is conducted under the following conditions:

| | |
|---|---|
| Injection molding temperature | Predetermined temperature indicated in each of the examples |
| Injection molding time | 5 Seconds |
| Residence time | 3 Seconds |
| Cooling time | 40 Seconds |
| Mold temperature | 80° C. |

EXAMPLE 1

(A) Benzaldehyde (212 g; 2 mols), 270 g (1 mol) of a 70% aqueous solution of D-sorbitol, and 10 g of p-toluenesulfonic acid were placed in a reactor and reacted at a temperature of 60° C. with stirring. In the reactor, the viscosity of the mixture increased gradually, and 30 minutes later, the mixture jellied and the torque of the stirrer reached about 3 times the original torque. At this time, the amount of DBS formed was 20% of theory.

To the jelly-like reaction product obtained in the above first-stage reaction were added 400 g of a 10% aqueous solution of hydrochloric acid and 100 g of water for shift to the second stage of the reaction. The temperature within the reactor was lowered to 25° C., and at this temperature, stirring was continued for 6 hours. The resulting suspension was treated with a 10% aqueous solution of sodium hydroxide, the catalyst was neutralized, and the resultant product was filtered off by a filter press, washed with water and dried to obtain 220 g of a white powder of DBS having a purity of about 90% (melting point: 182° to 187° C.). Its yield was about 55% of the theoretical value. The attached drawing shows its NMR spectrum.

(B) Reaction product as a suspension of DBS was obtained in the same way as in part (A) above, and it was further allowed to stand for 12 hours at ordinary temperature for aging to afford 280 g (about 70% of the theoretical value) of DBS having a purity of about 90% which was a similar product to the product obtained in (A).

EXAMPLES 2 to 5

Production of DBS was carried out in the same manner as in part (B) of Example 1, except that the catalyst used was replaced by the catalyst shown in Table 1 below. As a result, DBS having a purity of about 90%, similar to that in part (B) of Example 1, was obtained in the yield (based on the theoretical value) shown in Table 1.

TABLE 1

| Example No. | First stage Catalyst | Amount (g) | Second stage Catalyst | Amount (g) | Yield |
|---|---|---|---|---|---|
| 2 | concentrated (35%) hydrochloric acid | 30 | 10% hydrochloric acid | 400 | 77 |
| 3 | p-toluenesulfonic acid | 10 | 10% p-toluenesulfonic acid | 400 | 60 |
| 4 | 80% sulfuric acid | 10 | 10% sulfuric acid | 400 | 68 |
| 5 | tripolyphosphoric acid | 8 | 10% hydrochloric acid | 400 | 71 |

It was confirmed from its NMR spectrum that DBS obtained in each of the above-described examples was the same as DBS of Example 1.

EXAMPLE 6

The TBS-containing DBS obtained in part (B) of Example 1 was added in a predetermined amount to pellets of polyethylene having an average molecular weight of 60,000 (MITSUBISHI NOVATEC ET010, a product of Mitsubishi Petrochemical Co., Ltd.), and they were mixed by a blender to form a resin composition. The resin composition was injection molded at an injection molding temperature of 210° C. to prepare a test piece.

The constituents of the resin composition and the haze value and shrinkage of the test piece are shown in Table 2.

TABLE 2

| Composition No. | Constituents | | Physical properties | |
|---|---|---|---|---|
| | TBS/DBS mixture (part) | Polyethylene (part) | Haze value (%) | Shrinkage (%) |
| 6-1 | — | 100 | 77 | 15.3 |
| 6-2 | 0.2 | 99.8 | 56 | 7.8 |
| 6-3 | 0.3 | 99.7 | 28 | 4.8 |
| 6-4 | 0.5 | 99.5 | 28 | 2.6 |

EXAMPLE 7

A mixture of TBS and DBS in a weight ratio of 20:80 was added in a predetermined amount to pellets of an ethylene/propylene copolymer having a number-average molcular weight of 40,000 and a propylene units content of 90 mole% (MITSUBISHI NOBLEN BC-8, a product of Mitsubishi Petrochemical Co., Ltd.), and they were mixed by a blender to form a resin composition. The resin composition was injection molded at an injection molding temperature of 210° C. to prepare a test piece. The constituents of the resin composition and the haze value and shrinkage of the test piece are shown in Table 3.

TABLE 3

| Composition No. | Constituents | | Physical properties | |
|---|---|---|---|---|
| | TBS/DBS mixture (part) | Ethylene/propylene copolymer (part) | Haze value (%) | Shrinkage (%) |
| 7-1 | — | 100 | 80 | 13.9 |
| 7-2 | 0.2 | 99.8 | 55 | 10.8 |
| 7-3 | 0.3 | 99.7 | 49 | 6.3 |
| 7-4 | 0.5 | 99.5 | 39 | 2.1 |

EXAMPLE 8

A mixture of TBS and DBS in a weight ratio of 30:70 was added in a predetermined amount to pellets of polyethylene having an average molecular weight of 20,000 (SUMITOMO POLYETHYLENE G806, a product of Sumitomo Chemical Co., Ltd.), and they were mixed by a blender to make a resin composition. The resin composition was injection molded at an injection molding temperature of 180° C. to prepare a test piece.

The constituents of the resin composition and the haze value and shrinkage of the test piece are shown in Table 4.

TABLE 4

| Composition No. | Constituents | | Physical properties | |
|---|---|---|---|---|
| | TBS/DBS mixture (part) | Polyethylene (part) | Haze value (%) | Shrinkage (%) |
| 8-1 | — | 100 | 70 | 13.2 |
| 8-2 | 0.2 | 99.8 | 45 | 7.2 |
| 8-3 | 0.3 | 99.7 | 22 | 5.5 |
| 8-4 | 0.5 | 99.5 | 23 | 2.8 |

What is claimed is:

1. In a process for preparing dibenzylidenesorbitol by dehydrocondensation of 1 mol of sorbitol with 2 mols of benzaldehyde in the presence of an acid catalyst, the improvement in which the reaction is carried out in two stages; the first-stage reaction comprising reacting, at a temperature of 50° to 70° C., benzaldehyde with an aqueous solution of sorbitol having a sorbitol concentration of at least 70%, in the presence of 0.03 to 0.5 part by weight of an acid catalyst per part by weight of sorbitol; the first-stage reaction being shifted to the second-stage reaction by adding water, as a reaction medium, and an additional amount of an acid catalyst to the first-stage reaction mixture when the conversion of sorbitol to dibenzylidenesorbitol reaches 10 to 40% in the first-stage reaction, the amount of the added water being such that the amount of water in the reaction system during the second-stage reaction is at least 2.5 parts by weight per part by weight of sorbitol charged to the first-stage reaction, the amount of the additional acid catalyst being 0.02 to 0.5 part by weight per part by weight of sorbitol charged to the first stage-reaction; the second-stage reaction comprising reacting the resultant mixture in the suspended state at a temperature of 15° to 25° C.; the resulting dibenzylidenesorbitol being obtained as an aqueous suspension thereof.

2. The process of claim 1 wherein the amount of the added water is such that the amount of water in the reaction system during the second-stage reaction is 3 to 5 parts by weight per part by weight of sorbitol charged to the first-stage reaction.

3. The process of claim 1 wherein the catalyst is hydrochloric acid.

4. The process of claim 1 wherein the aqueous suspension of dibenzylidenesorbitol obtained by the second-stage reaction is subjected to aging.

5. The process of claim 1 wherein the first-stage reaction and the second-stage reaction are performed with stirring, and the time when the first-stage reaction is shifted to the second stage reaction is judged by an increase in the torque of the stirrer.

* * * * *

UNITED STATES PATENT AND TRADEMARK OFFICE
CERTIFICATE OF CORRECTION

PATENT NO. : 4,267,110
DATED : May 12, 1981
INVENTOR(S) : Hiroshi Uchiyama

It is certified that error appears in the above-identified patent and that said Letters Patent are hereby corrected as shown below:

On the cover page of the patent, in the space provided for foreign application priority data, section "[30]", change the application number for the Japanese application filed May 30, 1979 from "54-661036" to --54-66036--.

Signed and Sealed this

Nineteenth Day of January 1982

[SEAL]

Attest:

Attesting Officer

GERALD J. MOSSINGHOFF

Commissioner of Patents and Trademarks